United States Patent [19]

Bartmann et al.

[11] Patent Number: 5,188,759
[45] Date of Patent: Feb. 23, 1993

[54] HALOACETYLENE DERIVATIVES

[75] Inventors: Ekkehard Bartmann, Erzhausen; Reinhard Hittich, Modautal; Herbert Plach, Darmstadt; Ulrich Finkenzeller, Plankstadt, all of Fed. Rep. of Germany

[73] Assignee: Merck Patent Gesellschaft mit Beschrankter Haftung, Darmstadt, Fed. Rep. of Germany

[21] Appl. No.: 648,627

[22] Filed: Feb. 1, 1991

[30] Foreign Application Priority Data

Feb. 2, 1990 [DE] Fed. Rep. of Germany ....... 4003340
Aug. 30, 1990 [DE] Fed. Rep. of Germany ....... 4027458

[51] Int. Cl.$^5$ ..................... C09K 19/52; C09K 19/32; C09K 19/30; C07C 69/76
[52] U.S. Cl. ..................... 252/299.01; 252/299.62; 252/299.63; 252/299.64; 252/299.65; 558/17; 560/102; 568/58; 568/631; 568/647; 570/128; 570/185
[58] Field of Search ................... 568/58, 631, 647; 570/128, 185; 558/17; 560/102; 564/248; 252/299.01, 299.62, 299.63, 299.64, 299.65

[56] References Cited

U.S. PATENT DOCUMENTS

| | | | |
|---|---|---|---|
| 3,113,068 | 12/1963 | Woitz et al. ................... | 570/185 |
| 4,510,069 | 4/1985 | Eidenschink et al. ......... | 252/299.61 |
| 4,533,488 | 8/1985 | Fukui et al. ................... | 252/299.61 |
| 4,623,477 | 11/1986 | Ogawa et al. ................. | 252/299.5 |
| 4,632,515 | 12/1986 | Gray et al. .................... | 350/350 R |
| 4,657,695 | 4/1987 | Saito et al. .................... | 252/299.61 |
| 4,659,502 | 4/1987 | Fearon et al. ................. | 252/299.61 |
| 4,684,477 | 8/1987 | Sugimori et al. .............. | 252/299.61 |
| 4,704,227 | 11/1987 | Krause et al. ................. | 252/299.61 |
| 4,713,197 | 12/1987 | Eidenschink et al. ......... | 252/299.61 |
| 4,834,904 | 5/1989 | Krause et al. ................. | 252/299.01 |

OTHER PUBLICATIONS

Ackermann, Chemical Abstract 98(3) #16462c.

Primary Examiner—Mukund J. Shah
Assistant Examiner—Y. N. Gupta
Attorney, Agent, or Firm—Millen, White, Zelano and Branigan

[57] ABSTRACT

The invention relates to a liquid crystalline medium having at least two components, where at least one component is a haloacetylene derivatives of the formula I $$R^1-A^1-Z^1-(A^2-Z^2)_m-A^3-C\equiv C-X \qquad I$$

wherein
$R^1$ is an alkyl or alkenyl radical having up to 15 carbon atoms which is unsubstituted or monosubstituted by CN, halogen or CF$_3$, or such a radical wherein one or more CH$_2$ groups is replaced, in each case independently of one another, by —S—, —O—,

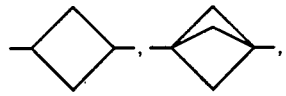

—CO—, —CO—O—, —O—CO— or —O—CO—O— in such a manner that sulfur and/or oxygen atoms are not linked directly to one another,
$A^1$, $A^2$ and $A^3$, in each case independently of one another, are
(a) a trans-1,4-cyclohexylene radical or —S— one or more non-adjacent CH$_2$ groups is replaced by —O— and/or —S—,
(b) a 1,4-phenylene radical N" in which one or two CH groups is replaced by N,
(c) 1,3-cyclobutylene, 1,3-bicyclo(1,1,1)pentylene, 1,4-cyclohexenylene, 1,4-bicyclo(2,2,2)octylene, naphthalene-2,6-diyl, decahydronaphthalene-2,6-diyl and 1,2,3,4-tetrahydronaphthalene-2,6-diyl,
$Z^1$ and $Z^2$ independently of one another, are —CH$_2$CH$_2$—, —C≡C—, —CH$_2$O—, —OCH$_2$—, —CO—O—, —O—CO—, —CH=N—, —N=CH—, —CH$_2$S—, —SCH$_2$—, a single bond or an alkylene group having 3 to 6 carbon atoms in which one CH$_2$ group may be replaced by —O—, —CO—O—, —O—CO—, —CH halogen— or —CHCN—,
X is F, Cl, —NCS, Br, —OCF$_3$ or —SCF$_3$, and
m is 0, 1 or 2.

7 Claims, No Drawings

HALOACETYLENE DERIVATIVES

SUMMARY OF THE INVENTION

The invention relates to holoacetylene derivatives of the formula I $$R^1-A^1-Z^1-(A^2-Z^2)_m-A^3-C\equiv C-X \quad \text{I}$$

where $R^1$ is an alkyl or alkenyl radical having up to 15 carbon atoms which is unsubstituted or monosubstituted by CN, halogen or $CF_3$, it also being possible for one or more $CH_2$ groups in these radicals to be replaced, in each case independently of one another, by —S—, —O—,

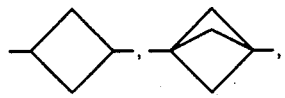

—CO—, —CO—O—, —O—CO— or —O—CO—O— in such a manner that sulphur and/or oxygen atoms are not linked directly to one another, $A^1$, $A^2$ and $A^3$, in each case independently of one another, are (a) a trans-1,4-cyclohexylene radical in which, in addition, one or more non-adjacent $CH_2$ groups may be replaced by —O— and/or —S—, (b) a 1,4-phenylene radical in which, in addition, one or two CH groups may be replaced by N, (c) a radical from the group comprising 1,3-cyclobutylene, 1,3-bicyclo(1,1,1)pentylene, 1,4-cyclohexenylene, 1,4-bicyclo(2,2,2)octylene, piperidine-1,4-diyl, naphthalene-2,6-diyl, decahydronaphthalene-2,6-diyl and 1,2,3,4-tetrahydronaphthalene-2,6-diyl, it being possible for the radicals (a) and (b) to be substituted by CN or halogen, $Z^1$ and $Z^2$ initially independently of one another, are —$CH_2CH_2$—, —C≡C—, —$CH_2O$—, —$OCH_2$—, —CO—O—, —O—CO—, —CH=N—, —N=CH—, —$CH_2S$—, —$SCH_2$—, a single bond or an alkylene group having 3 to 6 carbon atoms in which, in addition, one $CH_2$ group may be replaced by —O—, —CO—O—, —O—CO—, —CHhalogen— or —CHCN—, X is F, Cl, —NCS, Br, —$OCF_3$ or —$SCF_3$, and m is 0, 1 or 2.

The invention furthermore relates to the use of these compounds as components of liquid-crystalline media, and to liquid-crystal and electrooptical display elements which contain the liquid-crystalline media according to the invention.

The compounds of the formula I can be used as components of liquid-crystalline media, in particular for displays based on the principle of the twisted cell, including highly twisted variants thereof, such as, for example, STN or SBE, the guest-host effect, the effect of deformation of aligned phases or the effect of dynamic scattering.

The invention had the object of finding novel stable liquid-crystalline or mesogenic compounds which are suitable as components of liquid-crystalline media and in particular have comparatively low viscosity and a moderate positive dielectric anisotropy.

It has now been found that compounds of the formula I are eminently suitable as components of liquid-crystalline phases. In particular, they have comparatively low viscosities. Using them, stable liquid-crystalline phases which have a broad mesophase range, advantageous values for the optical and dielectric anisotropy and are at the same time distinguished by very favorable values for the specific resistance can be obtained. This gives considerable advantages, in particular in the case of media for active matrix displays or supertwist displays.

Similar compounds having liquid-crystalline properties with terminal groups containing an —C≡C—CN group have already been disclosed, for example in German Offenlegungsschrift 32 46 440.

Furthermore, JP 61/263,933 discloses similar compounds containing a terminal —C≡C-alkyl group.

However, there is no indication in these published applications of how the compounds of the formula I according to the invention can be prepared.

In addition, the provision of the compounds of the formula I very generally considerably extends the range of liquid-crystalline substances which are suitable, from various applicational points of view, for the preparation of liquid-crystalline mixtures.

The compounds of the formula I have a broad field of application. Depending on the choice of substituents, these compounds can be used as base materials from which liquid-crystalline phases are predominantly composed; however, compounds of the formula I can also be added to liquid-crystalline base materials from other classes of compound, in order, for example, to influence the dielectric and/or optical anisotropy of a dielectric of this type and/or to optimize its threshold voltage and/or its viscosity.

In the pure state, the compounds of the formula I are colorless and form liquid-crystalline mesophases in a very favorable temperature range for electrooptical use. They are stable chemically, thermally and to light.

The invention thus relates to the compounds of the formula I, in particular those in which $R^1$ is an alkyl radical having 1 to 15 C atoms, and/or in which X is F or Cl, and those in which at least one of the radicals $A^1$, $A^2$ and $A^3$ is optionally fluorine-substituted 1,4-phenylene, 1,4-cyclohexylene, pyrimidine-2,5-diyl or pyridine-2,5-diyl, in particular preferred are those wherein $A^3$ is 1,4-cyclohexylene.

The invention furthermore relates to the use of these compounds as components of liquid-crystalline media. The invention furthermore relates to liquid-crystalline media containing at least one compound of the formula I, and to liquid-crystal displays, in particular electrooptical displays, which contain media of this type.

For reason of simplicity, L below is —C≡C—, Cyc is a 1,4-cyclohexylene radical, Che is a 1,4-cyclohexenylene radical, Dio is a 1,3-dioxane-2,5-diyl radical, Dit is a 1,3dithiane-2,5-diyl radical, Phe is a 1,4-phenylene radical, Pyd is a pyridine-2,5-diyl radical, Pyr is a pyrimidine-2,5-diyl radical and Bi is a bicyclo(2,2,2)octylene radical, where Cyc and/or Phe may be unsubstituted or monosubstituted or disubstituted by F or CN.

Accordingly, the compounds of the formula I include dinuclear compounds of the sub-formulae Ia to Ib:

$$R^1-A^1-A^2-L-X \quad \text{Ia}$$

$$R^1-A^1-Z^1-A^2-L-X \quad \text{Ib}$$

Trinuclear compounds of the sub-formulae Ic to If:

| | |
|---|---|
| $R^1-A^1-A^1-A^2-L-X$ | Ic |
| $R^1-A^1-Z^1-A^1-Z^1-A^2-L-X$ | Id |
| $R^1-A^1-Z^1-A^1-A^2-L-X$ | Ie |
| $R^1-A^1-A^1-Z^1-A^2-L-X$ | If | and tetranuclear compounds of the sub-formulae Ig to In:

| | |
|---|---|
| $R^1-A^1-A^1-A^1-A^2-L-X$ | Ig |
| $R^1-A^1-Z^1-A^1-A^1-A^2-L-X$ | Ih |
| $R^1-A^1-A^1-Z^1-A^1-A^2-L-X$ | Ii |
| $R^1-A^1-A^1-A^1-Z-A^2-L-X$ | Ij |
| $R^1-A^1-Z^1-A^1-Z^1-A^1-A^2-L-X$ | Ik |
| $R^1-A^1-Z^1-A^1-A^1-Z^1-A^2-L-X$ | Il |
| $R^1-A^1-A^1-Z^1-A^1-Z^1-A^2-L-X$ | Im |
| $R^1-A^1-Z^1-A^1-Z^1-A^1-Z^2-A^2-L-X$ | In |

Of these, those of the sub-formulae Ia, Ib, Ic, Id, Ie, If, Ig, Ih, Ii and Il are particularly preferred. include those of the sub-formulae Iaa to Iah:

| | |
|---|---|
| $R^1$-Phe-Phe-L-X | Iaa |
| $R^1$-Phe-Cyc-L-X | Iab |
| $R^1$-Dio-Phe-L-X | Iac |
| $R^1$-Pyr-Phe-L-X | Iad |
| $R^1$-Pyd-Phe-L-X | Iae |
| $R^1$-Cyc-Phe-L-X | Iaf |
| $R^1$-Cyc-Cyc-L-X | Iag |
| $R^1$-Che-Phe-L-X | Iah |

Of these, those of the formulae Iaa, Iab, Iac, Iad, Iaf and Iag are particularly preferred.

The preferred compounds of the sub-formula Ib include those of the sub-formulae Iba to Ibm:

| | |
|---|---|
| $R^1$-Phe-$CH_2CH_2$-Phe-L-X | Iba |
| $R^1$-Phe-$OCH_2$-Phe-L-X | Ibb |
| $R^1$-Cyc-$CH_2CH_2$-Phe-L-X | Ibc |
| $R^1$-Cyc-$CH_2$-$CH_2$-Cyc-L-X | Ibd |
| $R^1$-Cyc-COO-Phe-L-X | Ibe |
| $R^1$-Cyc-COO-Cyc-L-X | Ibf |
| $R^1$-$A^1$-$CH_2CH_2$-Phe-L-X | Ibg |
| $R^1$-$A^1$-$CH_2CH_2$-Cyc-L-X | Ibh |
| $R^1$-$A^1$-$CH_2O$-Phe-L-X | Ibi |
| $R^1$-$A^1$-$OCH_2$-Phe-L-X | Ibj |
| $R^1$-$A^1$-COO-Phe-L-X | Ibk |
| $R^1$-$A^1$-OCO-Phe-L-X | Ibl |
| $R^1$-Che-$CH_2CH_2$-Phe-L-X | Ibm |

The preferred compounds of the sub-formula Ic include those of the sub-formulae Ica to Icm:

| | |
|---|---|
| $R^1$-Phe-Phe-Phe-L-X | Ica |
| $R^1$-Phe-Phe-Cyc-L-X | Icb |
| $R^1$-Phe-Dio-Phe-L-X | Icc |
| $R^1$-Cyc-Cyc-Phe-L-X | Icd |
| $R^1$-Cyc-Cyc-Cyc-L-X | Ice |
| $R^1$-Pyd-Phe-Phe-L-X | Icf |
| $R^1$-Pyr-Phe-Phe-L-X | Icg |
| $R^1$-Phe-Pyr-Phe-L-X | Ich |
| $R^1$-Cyc-Phe-Phe-L-X | Ici |
| $R^1$-Cyc-Phe-Cyc-L-X | Icj |
| $R^1$-Dio-Phe-Phe-L-X | Ick |
| $R^1$-Che-Phe-Phe-L-X | Icl |
| $R^1$-Phe-Che-Phe-L-X | Icm |

Of these, those of the formulae Ica, Icc, Icd, Ice, Ici and Icj are particularly preferred.

The preferred compounds of the sub-formula Id include those of the sub-formulae Ida to Idm:

| | |
|---|---|
| $R^1$-Phe-$Z^1$-Phe-$Z^1$-Phe-L-X | Ida |
| $R^1$-Phe-$Z^1$-Phe-$Z^1$-Cyc-L-X | Idb |
| $R^1$-Phe-$Z^1$-Dio-$Z^1$-Phe-L-X | Idc |
| $R^1$-Cyc-$Z^1$-Cyc-$Z^1$-Phe-L-X | Idd |
| $R^1$-Cyc-$Z^1$-Cyc-$Z^1$-Cyc-L-X | Ide |
| $R^1$-Pyd-$Z^1$-Phe-$Z^1$-Phe-L-X | Idf |
| $R^1$-Phe-$Z^1$-Pyd-$Z^1$-Phe-L-X | Idg |
| $R^1$-Pyr-$Z^1$-Phe-$Z^1$-Phe-L-X | Idh |
| $R^1$-Phe-$Z^1$-Pyr-$Z^1$-Phe-L-X | Idi |
| $R^1$-Phe-$Z^1$-Cyc-$Z^1$-Phe-L-X | Idj |
| $R^1$-Cyc-$Z^1$-Phe-$Z^1$-Cyc-L-X | Idk |
| $R^1$-Dio-$Z^1$-Phe-$Z^1$-Phe-L-X | Idl |
| $R^1$-Che-$Z^1$-Phe-$Z^1$-Phe-L-X | Idm |

The preferred compounds of the sub-formula Ie include those of the sub-formulae Iea to Iek:

| | |
|---|---|
| $R^1$-Pyr-$Z^1$-Phe-Phe-L-X | Iea |
| $R^1$-Dio-$Z^1$-Phe-Phe-L-X | Ieb |
| $R^1$-Cyc-$Z^1$-Phe-Phe-L-X | Iec |

| | |
|---|---|
| R¹-Cyc-Z¹-Phe-Cyc-L-X | Ied |
| R¹-Phe-Z¹-Cyc-Phe-L-X | Iee |
| R¹-Cyc-Z¹-Cyc-Phe-L-X | Ief |
| R¹-Cyc-Z¹-Cyc-Cyc-L-X | Ieg |
| R¹-Phe-Z¹-Dio-Phe-L-X | Ieh |
| R¹-Pyd-Z¹-Phe-Phe-L-X | Iei |
| R¹-Phe-Z¹-Pyr-Phe-L-X | Iej |
| R¹-Phe-Z¹-Che-Phe-L-X | Iek |

The preferred compounds of the sub-formula If include those of the sub-formulae Ifa to Ifp:

| | |
|---|---|
| R¹-Pyr-Phe-Z¹-Phe-L-X | Ifa |
| R¹-Pyr-Phe-OCH₂-Phe-L-X | Ifb |
| R¹-Phe-Phe-Z¹-Phe-L-X | Ifc |
| R¹-Phe-Phe-Z¹-Cyc-L-X | Ifd |
| R¹-Cyc-Cyc-Z¹-Phe-L-X | Ife |
| R¹-Cyc-Cyc-Z¹-Cyc-L-X | Iff |
| R¹-Cyc-Cyc-CH₂CH₂-Phe-L-X | Ifg |
| R¹-Pyd-Phe-Z¹-Phe-L-X | Ifh |
| R¹-Dio-Phe-Z¹-Phe-L-X | Ifi |
| R¹-Phe-Cyc-Z¹-Phe-L-X | Ifj |
| R¹-Phe-Cyc-Z¹-Cyc-L-X | Ifk |
| R¹-Phe-Pyd-Z¹-Phe-L-X | Ifl |
| R¹-Che-Phe-Z¹-Phe-L-X | Ifm |
| R¹-Phe-Che-Z¹-Phe-L-X | Ifn |
| R¹-Cyc-Phe-Z¹-Phe-L-X | Ifo |
| R¹-Cyc-Phe-Z¹-Cyc-L-X | Ifp |

The preferred compounds of the formula Ig include those of the formulae Iga to Igf:

| | |
|---|---|
| R¹-Phe-Phe-Phe-Phe-L-X | Iga |
| R¹-Cyc-Phe-Phe-Phe-L-X | Igb |
| R¹-Cyc-Cyc-Phe-Phe-L-X | Igc |
| R¹-Cyc-Cyc-Cyc-Phe-L-X | Igd |
| R¹-Cyc-Cyc-Cyc-Cyc-L-X | Ige |
| R¹-Cyc-Phe-Phe-Cyc-L-X | Iga |

The terminal group L—X includes the groups of the formulae 1 to 6:

| | |
|---|---|
| C≡C—Cl | 1 |
| C≡C—F | 2 |
| C≡C—Br | 3 |
| C≡C—OCF₃ | 4 |
| C≡C—SCF₃ | 5 |
| C≡C—NCS | 6 |

$R^1$ is preferably alkyl, furthermore alkoxy. $A^1$, $A^2$ and/or $A^3$ are preferably Phe, Cyc, Che, Pyr or Dio. The compounds of the formula I preferably contain not more than one of the radicals Bi, Pyd, Pyr, Dio or Dit.

Preferred compounds of the formula I and of all the sub-formulae are those in which $A^1$, $A^2$ and/or $A^3$ are 1,4-phenylene which is monosubstituted or disubstituted by F or monosubstituted by CN. These are, in particular, 2-fluoro-1,4-phenylene, 3-fluoro-1,4-phenylene and 2,3-difluoro-1,4-phenylene, and 2-cyano-1,4-phenylene and 3-cyano-1,4-phenylene.

$Z^1$ and $Z^2$ are preferably a single bond, —CO—O—, —O—CO— and —CH₂CH₂—, and secondarily preferably —CH₂O— and —OCH₂—.

If $R^1$ is an alkyl radical and/or an alkoxy radical, it may be straight-chain or branched. It is preferably straight-chain, has 2, 3, 4, 5, 6 or 7 C atoms and is accordingly preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If $R^1$ is an alkenyl radical, it may be straight-chain or branched. It is preferably straight-chain and has 2 to 10 C atoms. It is accordingly particularly vinyl, prop-1- or -2-enyl, but-1-, -2- or -3-enyl, pent-1-, -2-, -3- or -4-enyl, hex-1-, -2-, -3-, -4-or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If $R^1$ is an alkyl radical in which one CH₂ group has been replaced by —O— and one has been replaced by —CO—, these are preferably adjacent. These thus contain an acyloxy group —CO—O— or an oxycarbonyl group —O—CO—. These are preferably straight-chain and have 2 to 6 C atoms. They are accordingly particularly acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl and 4-(methoxycarbonyl)butyl.

If $R^1$ is an alkenyl radical in which one CH₂ group has been replaced by CO or CO—O or O—CO, it may be straight-chain or branched. It is preferably straight-chain and has 4 to 13 C atoms. It is accordingly particularly acryloyloxymethyl, 2-acryloyloxyethyl, 3- acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

Compounds of the formula I which contain wing groups $R^1$ which are suitable for polymerization reactions are suitable for the preparation of liquid-crystalline polymers.

Compounds of the formula I containing branched wing groups $R^1$ and/or Q—X may occasionally be of importance due to better solubility in the customary liquid-crystalline base materials, but in particular as chiral dopes if they are optically active. Smectic compounds of this type are suitable as components of ferroelectric materials.

Compounds of the formula I having $S_A$ phases are suitable, for example, for thermally addressed displays.

Branched groups of this type generally contain not more than one chain branch. Preferred branched radicals $R^1$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 4-methylhexyl, 2-nonyl, 2-decyl, 2-dodecyl, 6-methyloctoxy, 6-methyloctaroyloxy, 5-methylheptyloxycarbonyl, 2-methylbutyryloxy, 3-methylvaleryloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl and 2-methyl-3-oxahexyl.

Preferred branched radicals Q-X are in particular 1,2,2-trifluoro-2-chloroethyl, 1,1,2-trifluoro-2-chloroethyl, 1,2-difluoro-2-chloroethyl or 1,2,2-trifluoro-2-cyanoethyl.

If $R^1$ is an alkyl radical in which two or more $CH_2$ groups have been replaced by —O— and/or —CO—O—, it may be straight-chain or branched. It is preferably branched and has 3 to 12 C atoms. It is accordingly particularly biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)-ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl or 5,5-bis(ethoxycarbonyl)hexyl.

Compounds of the formula I which contain wing groups $R^1$ which are suitable for polycondensations are suitable for the preparation of liquid-crystalline polycondensates.

The formula I covers the racemates of these compounds and the optical antipodes, and mixtures thereof.

Of these compounds of the formula I and the subformulae, those are preferred in which at least one of the radicals present therein has one of the preferred meanings indicated.

In the compounds of the formula I, those stereoisomers in which the rings Cyc and piperidine are trans-1,4-disubstituted are preferred. Those of the above-mentioned formulae which contain one or more groups Pyd, Pyr and/or Dio in each case include the two 2,5-positional isomers.

Particularly preferred compounds of the formula I which contain a group of the formula 1 are those of the sub-formulae I1a to I1p:

| | |
|---|---|
| alkyl-Cyc-Phe-C≡C-Cl | I1a |
| alkyl-Phe-Phe-C≡C-Cl | I1b |
| alkyl-Cyc-Cyc-Phe-C≡C-Cl | I1c |
| alkyl-Cyc-Phe-Phe-C≡C-Cl | I1d |
| alkyl-Cyc-Ch₂Ch₂-Phe-C≡C-Cl | I1e |
| alkyl-Phe-CH₂CH₂-Phe-C≡C-Cl | I1f |
| alkyl-Phe-CO-O-Phe-C≡C-Cl | I1g |
| alkyl-Cyc-CO-O-Phe-C≡C-Cl | I1h |
| alkyl-cyc-Phe-c≡C-Phe-C≡C-Cl | I1i |
| alkyl-Cyc-Phe-CH₂CH₂-Phe-C≡C-Cl | I1j |
| alkyl-Cyc-Cyc-CH₂CH₂-Phe-C≡C-Cl | I1k |
| alkyl-Phe-Phe-CH₂CH₂-Phe-C≡C-Cl | I1l |
| alkyl-Cyc-CH₂CH₂-Cyc-Phe-C≡C-Cl | I1m |
| alkyl-Cyc-Cyc-C≡C-Cl | I1n |
| alkyl-CYC-ch₂ch₂-cYC-c≡C-CL | i1o |
| alkyl-Cyc-CO-O-Cyc-C≡C-Cl | I1p |

Particularly preferred compounds of the formula I which contain a group of the formula 2 are those of the sub-formulae I2a to I2q:

| | |
|---|---|
| alkyl-Phe-Phe-C≡C-F | I2a |
| alkyl-Cyc-Phe-C≡C-F | I2b |
| alkyl-Cyc-Phe-Phe-C≡C-F | I2c |
| alkyl-Cyc-Cyc-Phe-C≡C-F | I2d |
| alkyl-Phe-Phe-Phe-C≡C-F | I2e |
| alkyl-Phe-CH₂CH₂-Phe-C≡C-F | I2f |
| alkyl-Cyc-CH₂CH₂-Phe-C≡C-F | I2g |
| alkyl-Cyc-CO-O-Phe-C≡C-F | I2h |
| alkyl-Phe-CO-O-Phe-C≡C-F | I2i |
| alkyl-Cyc-Phe-C≡C-Phe-C≡C-F | I2j |
| alkyl-Cyc-Phe-CH₂CH₂-Phe-C≡C-F | I2k |
| alkyl-Cyc-Cyc-CH₂CH₂-Phe-C≡C-F | I2l |
| alkyl-Phe-Phe-CH₂CH₂-Phe-C≡C-F | I2m |
| alkyl-Cyc-CH₂CH₂-Cyc-Phe-C≡C-F | I2n |

| | |
|---|---|
| alkyl-Cyc-Cyc-C≡C-F | I2o |
| alkyl-Cyc-CH₂CH₂-Cyc-C≡C-F | I2p |
| alkyl-Cyc-CO-O-Cyc-C≡C-F | I2q |

Particularly preferred compounds of the formula I which contain a group of the formula 4 are those of the sub-formulae I4a to I4q:

| | |
|---|---|
| alkyl-Phe-Phe-CHF-C≡C-OCF₃ | I4a |
| alkyl-Cyc-Phe-CHF-C≡C-OCF₃ | I4b |
| alkyl-Cyc-Phe-Phe-CHF-C≡C-OCF₃ | I4c |
| alkyl-Cyc-Cyc-Phe-CHF-C≡C-OCF₃ | I4d |
| alkyl-Phe-Phe-Phe-CHF-C≡C-OCF₃ | I4e |
| alkyl-Phe-CH₂CH₂-Phe-CHF-C≡C-OCF₃ | I4f |
| alkyl-Cyc-CH₂CH₂-Phe-CHF-C≡C-OCF₃ | I4g |
| alkyl-Cyc-CO-O-Phe-CHF-C≡C-OCF₃ | I4h |
| alkyl-Phe-CO-O-Phe-CHF-C≡C-OCF₃ | I4i |
| alkyl-Cyc-Phe-C≡C-Phe-CHF-C≡C-OCF₃ | I4j |
| alkyl-Cyc-Phe-CH₂CH₂-Phe-CHF-C≡C-OCF₃ | I4k |
| alkyl-Cyc-Cyc-CH₂CH₂-Phe-CHF-C≡C-OCF₃ | I4l |
| alkyl-Phe-Phe-CH₂CH₂-Phe-CHF-C≡C-OCF₃ | I4m |
| alkyl-Cyc-CH₂CH₂-Cyc-Phe-CHF-C≡C-OCF₃ | I4n |
| alkyl-Cyc-Cyc-C≡C-OCF₃ | I4o |
| alkyl-Cyc-CH₂CH₂-Cyc-C≡C-OCF₃ | I4p |
| alkyl-Cyc-CO-O-Cyc-C≡C-OCF₃ | I4q |

Particularly preferred compounds or the formula I which contain a group of the formula 6 are those of the formulae I6a to I6q:

| | |
|---|---|
| alkyl-Phe-Phe-C≡C-NCS | I6a |
| alkyl-Cyc-Phe-C≡C-NCS | I6b |
| alkyl-Cyc-Phe-Phe-C≡C-NCS | I6c |
| alkyl-Cyc-Cyc-Phe-C≡C-NCS | I6d |
| alkyl-Phe-Phe-Phe-C≡C-NCS | I6e |
| alkyl-Phe-CH₂CH₂-Phe-C≡C-NCS | I6f |
| alkyl-Cyc-CH₂CH₂-Phe-C≡C-NCS | I6g |
| alkyl-Cyc-CO-O-Phe-C≡C-NCS | I6H |
| alkyl-Phe-CO-O-Phe-C≡C-NCS | I6i |
| alkyl-Cyc-Phe-C≡C-Phe-C≡C-NCS | I6j |
| alkyl-Cyc-Phe-CH₂CH₂-Phe-C≡C-NCS | I6k |
| alkyl-Cyc-Cyc-CH₂CH₂-Phe-C≡C-NCS | I6l |
| alkyl-Phe-Phe-CH₂CH₂-Phe-C≡C-NCS | I6m |
| alkyl-Cyc-CH₂CH₂-Cyc-Phe-C≡C-NCS | I6n |
| alkyl-Cyc-Cyc-C≡C-NCS | I6o |
| alkyl-Cyc-CH₂CH₂-Cyc-C≡C-NCS | I6p |
| alkyl-Cyc-CO-O-Cyc-C≡C-NCS | I6q |

In the abovementioned compounds of the sub-formulae I1a to I1m, I2a to I2n, I4a to I4n and I6a to I6n, alkyl and alkyl groups each have from 1 to 12 carbon atoms.

The 1,4-cyclohexenylene group preferably has the following structures:

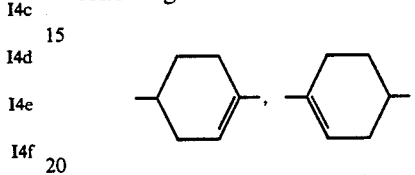

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart, Vol. IX, pp. 867 ff.), to be precise under reaction conditions which are known and suitable for the reactions mentioned. Use can also be made here of variants which are known per se, but are not described in great detail here.

The compounds according to the invention can be prepared in accordance with Scheme 1.

Scheme 1

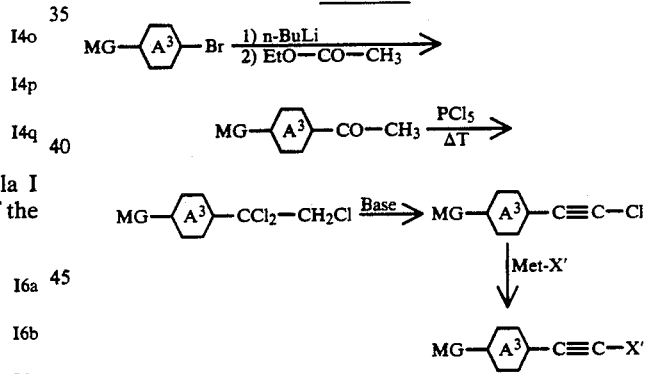

Met: Li, Na, K, Cs
MG above and below is a mesogenic group conforming to the formula $R^1$—$A^1$—$Z^1$—$(A^2$—$Z^2)_m$—.
$X'$ is F, Br, OCF₃, SCF₃ or NCS.

Scheme 2
($A^3$ = 1,4-Cyclohexylene)

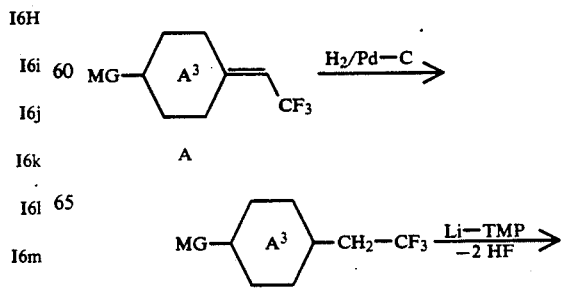

-continued
Scheme 2

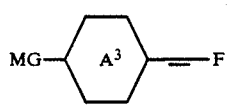

Li—TMP: N-Lithium-2,2,6,6-tetramethylpiperidin

The compounds of the formula A are prepared according German Offenlegungsschrift DE 40 02 411-A.

If desired, the starting materials can also be formed in situ by not isolating them from the reaction mixture, but instead immediately reacting them further to form the compounds of the formula I.

Thus, the compounds of the formula I can be prepared by reducing a compound which contains one or more reducible groups and/or C—C bonds in place of H atoms, but otherwise corresponds to the formula I.

Suitable reducible groups are preferably carbonyl groups, in particular keto groups, furthermore for example, free or esterified hydroxyl groups or aromatically bound halogen atoms. Preferred starting materials for the reduction correspond to the formula I, but can contain a cyclohexene ring or cyclohexanone ring in place of a cyclohexane ring and/or can contain a —CH=CH— group in place of a —CH$_2$CH$_2$— group and/or can contain a —CO— group in place of a —CH$_2$— group and/or can contain a free or functionally (for example in the form of its p-toluenesulfonate) derived OH group in place of an H atom.

The reduction can be carried out, for example, by catalytic hydrogenation at temperatures between about 0° and about 200° and at pressures between about 1 and 200 bar in an inert solvent, for example an alcohol, such as methanol, ethanol or isopropanol, an ether, such as catalytic hydrogenation at temperatures between about 0° and about 200° and at pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are preferably noble metals, such as Pt or Pd, which can be employed in the form of oxides (for example PtO$_2$ or PdO), on a support (for example Pd on charcoal, calcium carbonate or strontium carbonate) or in finely divided form.

Ketones can also be reduced by the methods of Clemmensen (using zinc, zinc amalgam or tin and hydrochloric acid, preferably in aqueous-alcoholic solution or in the heterogeneous phase with water/toluene at temperatures between about 80° and 120°) or Wolff-Kishner (using hydrazine, preferably in the presence of alkali, such as KOH or NaOH, in a high-boiling solvent, such as diethylene glycol or triethylene glycol, at temperatures between about 100° and 200°) to form the corresponding compounds of the formula I which contain alkyl groups and/or CH$_2$CH$_2$— bridges.

In addition, reductions using complex hydrides are possible. For example, arylsulfonyloxy groups can be removed reductively using LiAlH$_4$, in particular p-toluenesulfonyloxymethyl groups are reduced to methyl groups, preferably in an inert solvent, such as diethyl ether or THF, at temperatures between about 0° and 100°. Double bonds can be hydrogenated using NaBH$_4$ or tributyltin hydride in methanol.

Compounds of the formula I which contain 1,4-cyclohexenylene radicals in place of 1,4-phenylene radicals but otherwise correspond to the formula I can be oxidized, for example, using DDQ (dichlorodicyanobenzoquinone) in a suitable solvent.

Esters of the formula I can also be obtained by esterification of appropriate carboxylic acids (or reactive derivatives thereof) using alcohols or phenols (or reactive derivatives thereof) or by the DCC method (Smith, M. et al., J. Am. Chem. Soc. 80, 6204 (1958)).

Suitable reactive derivatives of the carboxylic acids mentioned are, in particular, the acyl halides, above all the chlorides and bromides, furthermore the anhydrides, for example also mixed anhydrides, azides or esters, in particular alkyl esters having 1–4 C atoms in the alkyl group.

Suitable reactive derivatives of the alcohols or phenols mentioned are, in particular, the corresponding metal alkoxides or phenoxides, preferably of an alkali metal such as sodium or potassium.

The esterification is advantageously carried out in the presence of an inert solvent. Highly suitable solvents are, in particular, ethers, such as diethyl ether, di-n-butyl ether, THF, dioxane or anisole, ketones, such as, for example, acetone, butanone or cyclohexanone, amides, such as, for example, DMF or hexamethylphosphoric triamide, hydrocarbons, such as, for example, benzene, toluene or xylene, halogenated hydrocarbons, such as, for example, tetrachloromethane, dichloromethane or tetrachloroethylene, and sulfoxides, such as, for example, dimethyl sulfoxide or sulfolane.

In order to prepare nitriles of the formula I, appropriate acid amides, for example those in which a CONH$_2$ group replaces the CN radical, can be dehydrated. The amides can be obtained, for example, from appropriate esters or acyl halides by reaction with ammonia. Suitable water-eliminating agents are, for example, inorganic acid chlorides, such as SOCl$_2$, PCl$_3$, PCl$_5$, POCl$_3$, SO$_2$Cl$_2$, COCl$_2$, furthermore P$_2$O$_5$, P$_2$S$_5$, AlCl$_3$ (for example as a double compound with NaCl), aromatic sulfonic acids and sulfonyl halides. The reaction can be carried out in the presence or absence of an inert solvent at temperatures between about 0° and 150°; suitable solvents are, for example, bases, such as pyridine or triethylamine, aromatic hydrocarbons, such as benzene, toluene or xylene, or amides, such as DMF.

To prepare the abovementioned nitriles of the formula I, it is also possible to react appropriate acyl halides, preferably the chlorides, with sulfamide, preferably in an inert solvent, such as, for example, tetramethylene sulfone, at temperatures between about 80° and 150°, preferably at 120°. After customary work-up, the nitriles can be isolated directly.

Ethers of the formula I can be obtained by etherification of corresponding hydroxyl compounds, preferably corresponding phenols, the hydroxyl compound expediently first being converted into a corresponding metal derivative, for example into the corresponding alkali metal alkoxide or alkali metal phenoxide by treatment with NaH, NaNH$_2$, NaOH, KOH, Na$_2$CO$_3$ or K$_2$CO$_3$. This can then be reacted with the appropriate alkyl halide, sulfonate or dialkyl sulfate, expediently in an inert solvent, such as, for example, acetone, 1,2-dimethoxyethane, DMF or dimethyl sulfoxide, or also with an excess of aqueous or aqueous-alcoholic NaOH or KOH, at temperatures between about 20° and 100°.

To prepare nitriles of the formula I, it is also possible to react appropriate chlorine, bromine or iodine compounds of the formula I with a cyanide, preferably with a metal cyanide, such as, for example, NaCN, KCN or Cu$_2$(CN)$_2$, for example in the presence of pyridine in an inert solvent, such as, for example, DMF or N-methylpyrrolidone, at temperatures between 20° and 200°.

Compounds of the formula I in which A$^1$ is substituted by at least one F atom and/or one CN group can also be obtained from the corresponding diazonium salts by replacement of the diazonium group by a fluorine atom or by a CN group, for example by the methods of Schiemann or Sandmeyer.

Dioxane derivatives and dithiane derivatives of the formula I are expediently prepared by reacting an appropriate aldehyde (or a reactive derivative thereof) with an appropriate 1,3-diol (or a reactive derivative thereof) or an appropriate 1,3-dithiol, preferably in the presence of an inert solvent, such as, for example, benzene or toluene, and/or in the presence of a catalyst, for example a strong acid such as: sulfuric acid, benzenesulfonic acid or p-toluenesulfonic acid, at temperatures presence of an inert solvent, such as, for example, benzene or toluene, and/or in the presence of a catalyst, for example a strong acid such as sulfuric acid, benzenesulfonic acid or p-toluenesulfonic acid, at temperatures between about 20° and about 150°, preferably between 80° and 120°. Suitable reactive derivatives of the starting materials are primarily acetals.

Some of the aldehydes, 1,3-diols and 1,3-dithiols mentioned, and some of the reactive derivatives thereof, are known, and some can be prepared without difficulties from compounds known from the literature by standard methods of organic chemistry. For example, the aldehydes can be obtained by oxidation of corresponding alcohols or by reduction of nitriles or corresponding carboxylic acids or derivatives thereof, the diols can be obtained by reduction of corresponding diesters, and the dithiols can be obtained by reaction of corresponding dihalides with NaSH.

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

R'—L—E—R''      1

R'—L—COO—E—R''      2

R'—L—OOC—E—R''      3

R'—L—CH$_2$CH$_2$—E—R''      4

R'—L—C≡C—E—R''      5

In the formulae 1, 2, 3, 4 and 5, L and E, which may be identical or different, are, in each case independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group comprising -Phe-Cyc-, -Cyc-Cyc-, -G-Phe- and -G-Cyc-.

In the compounds of the sub-formulae 1a, 2a, 3a, 4a and 5a, R' and R'' are, in each case independently of one another, alkyl, alkenyl, alkoxy, alkenyloxy or alkanoyloxy having up to 8 carbon atoms. In most of these compounds, R' and R'' are different from one another, one of these radicals usually being alkyl or alkenyl. In the compounds of the sub-formulae 1b, 2b, 3b, 4b and 5b, R'' is —CN, —CF$_3$, —OCF$_3$, —OCHF$_2$, F, Cl or —NCS; in this case, R has the meaning given for the compounds of the sub-formulae 1a to 5a and is preferably alkyl or alkenyl. However, other variants of the proposed substituents in the compounds of the formulae 1, 2, 3, 4 and 5 are common. Many such substances or alternatively mixtures thereof are commercially available. All these substances can be obtained by methods which are known from the literature or analogously thereto.

Besides components from the group comprising the compounds 1a, 2a, 3a, 4a and 5a (Group 1), the media according to the invention also contain components from the group comprising the compounds 1b, 2b, 3b, 4b and 5b (Group 2), whose proportions are preferably as follows:

Group 1: 20 to 90%, in particular 30 to 90%,
Group 2: 10 to 80%, in particular 10 to 50%,
the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding applications Federal Republic of Germany P 40 03 340.6, filed Feb. 2, 1990, and Federal Republic of German P 40 27 458.6, filed Aug. 30, 1990, are hereby incorporated by reference.

"Customary work-up" means that water is added, the mixture is extracted with methylene chloride, the organic phase is separated off, dried and evaporated, and the product is purified by crystallization and/or chromatography.

In addition, the abbreviations have the following meanings:
C: crystalline solid state, S: smectic phase (the index characterizes the phase type), N: nematic state, Ch: cholesteric phase, I: isotropic phase. The number between two symbols indicates the conversion temperature in degrees Celsius.
DAST: Diethylaminosulfur trifluoride
DCC: Dicyclohexylcarbodiimide
DDQ: Dichlorodicyanobenzoquinone
DIBALH: Diisobutylaluminum hydride
KOT: Potassium tertiary-butoxic
THF: Tetrahydrofuran
pTSOH: p-Toluenesulfonic acid

EXAMPLE 1

1-(2-Chloroethynyl)-2-(trans-4-pentylcyclohexyl)benzene

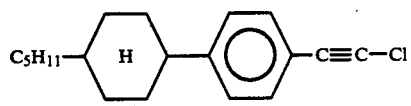

312.3 g (1.5 mol) of phosphorus pentachloride are added carefully to a solution of 172.4 g (1.0 mol) of methyl 4-(4-pentylcyclohexyl)phenyl ketone in 1.4 l of dichloromethane. The mixture is refluxed for 3 days and then poured onto ice; the organic phase is separated off, and the aqueous phase is extracted once with dichloromethane. The combined organic phases are evaporated on a rotary evaporator, and the residue, together with 263.2 g (2.34 mol) of potassium t-butoxide, is dissolved in 1.4 l of t-butanol. The mixture is refluxed for 15 hours and then evaporated on a rotary evaporator. The residue obtained is chromatographed on a silica gel column using petroleum ether as eluent. The eluate is evaporated on a rotary evaporator, and the product is recrystallized from petroleum ether (crystallization at −70° C.) and from 2-propanol. C 66N 70 I, $\eta$ (20° C.) 13 mm$^2$/sec, $\Delta$n 0.208, $\Delta_\epsilon$+6.7.

The following are prepared analogously:
1-(2-chloroethynyl)-4-(trans-4-propylcyclohexyl)benzene
1-(2-chloroethynyl)-4-(trans-4-heptylcyclohexyl)benzene
4'-(2-chloroethynyl)-4-(trans-4-propylcyclohexyl)biphenyl
4'-(2-chloroethynyl)-4-(trans-4-pentylcyclohexyl)biphenyl, C 152 S 215 I, $\Delta_\epsilon$+2.5.
4'-(2-chloroethynyl)-4-(trans-4-heptylcyclohexyl)biphenyl
1-(2-chloroethynyl)-4-(trans,trans-4'-propylbicyclohexyl-4-yl)benzene
1-(2-chloroethynyl)-4-(trans,trans-4'-pentylbicyclohexyl-4-yl)benzene
1-(2-chloroethynyl)-4-(trans,trans-4'-heptylbicyclohexyl-4-yl)benzene.

EXAMPLE 2

1-(2-Fluoroethynyl)-4-(trans-4-pentylcyclohexyl)benzene

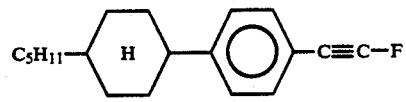

110 ml of 1 molar solution of tetrabutylammonium fluoride in dichloromethane are added at 0° C. to a solution of 28.85 g (0.1 mol) of 1-(2-chloroethynyl)-4-(trans-4-pentylcyclohexyl)benzene in 150 ml of dichloromethane. The reaction mixture is boiled for 24 hours and evaporated in vacuo, and the residue is then extracted with 3×150 ml of petroleum ether (30°-50° C.). The combined petroleum ether phases are dried over magnesium sulphate and evaporated. The product is obtained from the resultant residue by chromatography using petroleum ether as eluent.

The following are prepared analogously:
1-(2-fluoroethynyl)-4-(trans-4-propylcyclohexyl)benzene
1-(2-fluoroethynyl)-4-(trans-4-heptylcyclohexyl)benzene
4-(2-fluoroethynyl)-4'-(trans-4-propylcyclohexyl)biphenyl
4-(2-fluoroethynyl)-4'-(trans-4-pentylcyclohexyl)biphenyl
4-(2-fluoroethynyl)-4'-(trans-4-heptylcyclohexyl)biphenyl
1-(2-fluoroethynyl)-4-(trans,trans-4'-propylbicyclohexyl-4-yl)benzene 1-(2-fluoroethynyl)-4-(trans,trans-4'-pentylbicyclohex-yl-4-yl)benzene
1-(2-fluoroethynyl)-4-(trans,trans-4'-heptylbicyclohex-yl-4-yl)benzene.

EXAMPLE 3

4-trans,trans-(2-Fluoroethinyl)-4'-propylbicyclohexyl

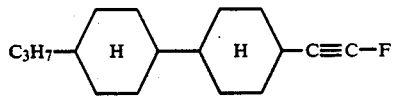

A solution of lithium-2,2,6,6-tetramethylpiperid [prepared from 12.3 g (105 mmol) of 2,2,6,6-tetramethylpiperidine in 50 ml of THF and 65 ml of a solution of n-butyllithium in n-hexane (15%)] is added at 0° C. to a solution of 13.9 g (50 mmol) trans,trans-4-propyl-4'-(2,2,2-trifluoroethyl)bicyclohexyl in 100 ml of THF. The reaction mixture is stirred for 24 hours at 0° C. and evaporated in vacuo. The residue is solved in 100 ml of cyclohexane, filtered and evaporated in vacuo. The residue is distilled in vacuo at 120°–130° C. ($10^{-4}$ mmHg).

EXAMPLE 4

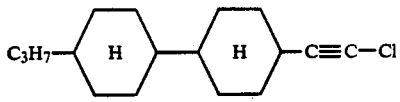

4-trans,trans-(2-Chloroethinyl)-4'-propylbicyclohexyl 4.0 g (94 mmol) of lithiumchloride are added to a solution of 11.9 g (50 mmol) of 4-trans,trans-(2-Fluoroethinyl)-4'-propylbicyclohexyl in 100 ml of THF. The reaction mixture is refluxed for 24 hours and evaporated in vacuo. The residue is purified by chromatography using silicagel and pentane as eluent. The eluate is evaporated in vacuo and the residue crystallized from hexane.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a liquid-crystalline medium having at least two components, the improvement wherein at least one component is a haloacetylene derivative of formula I:

$$R^1—A^1—Z^1—(A^2—Z^2)_m—A^3—C≡C—X$$

wherein:
R$^1$ is an alkyl or alkenyl radical having up to 15 carbon atoms which is unsubstituted or mono-substituted by CN, halogen or CF$_3$, or such a radical wherein one or more CH$_2$ groups is replaced, in each case independently of one another, by —S—, —O—,

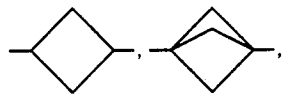

—CO—, —CO—O—, —O—CO, or —O—OC—O— in such a manner that sulfur and/or oxygen atoms are not linked directly to one another, A$^1$, A$^2$ and A$^3$, in each case independently of one another, are
(a) a trans-1,4-cyclohexylene radical or such a radical in which one or more non-adjacent CH$_2$ groups is replaced by —O— and/or —S—,
(b) a 1,4-phenylene radical
(c) 1,3-cyclohexenylene, 1,3-bicyclo(1,1,1) pentylene, 1,4-cyclohexylene, 1,4-bicyclo(2,2,2,)octylene, naphthalene-2,6-diyl, decahydronaphthalene-2,6-diyl and 1,2,3,4-tetrahydronaphthalene-2,6-diyl,
or a radical in (a) or (b) substituted by CN or halogen, Z$^1$ and Z$^2$ independently of one another, are —CH$_2$CH$_2$—, —C≡C, —CH$_2$O—, —OCH$_2$—, —CO—O—, —O—CO—, —CH=N, —N=CH—, —CH$_2$S—, —SCH$_2$—, a single bond or an alkylene group having 3 to 6 carbon atoms in which one CH$_2$ group may be replaced by —O—, —CO—O—, —O—CO—, —CHhalogen— or —CHCN—, X is F, Cl, —NCS, Br, —OCF$_3$ or —SCF$_3$, and m is 0, 1 or 2.

2. A derivative according to claim 1, wherein R$^1$ is an alkyl radical having 1 to 15 carbon atoms.

3. A derivative according to claim 1, wherein X is F or Cl.

4. A derivative according to claim 1, wherein at least one of the radicals A$^1$, A$^2$ and A$^3$ is 1,4-phenylene, 1,4-cyclohexylene, or one of the above substituted by fluorine.

5. A liquid crystalline medium according to claim 2, wherein at least one component is a compound selected from the sub-formulae IIa to IIp:

| | |
|---|---|
| alkyl-Cyc-Phe-C≡C-Cl | IIa |
| alkyl-Phe-Phe-C≡C-Cl | IIb |
| alkyl-Cyc-Cyc-Phe-C≡C-Cl | IIc |
| alkyl-Cyc-Phe-Phe-C≡C-Cl | IId |
| alkyl-Cyc-CH$_2$CH$_2$-Phe-C≡C-Cl | IIe |
| alkyl-Phe-CH$_2$CH$_2$-Phe-C≡C-Cl | IIf |
| alkyl-Phe-CO-O-Phe-C≡C-Cl | IIg |
| alkyl-Cyc-CO-O-Phe-C≡C-Cl | IIh |
| alkyl-Cyc-Phe-C≡C-Phe-C≡C-Cl | IIi |
| alkyl-Cyc-Phe-CH$_2$CH$_2$-Phe-C≡C-Cl | IIj |
| alkyl-Cyc-Cyc-CH$_2$CH$_2$-Phe-C≡C-Cl | IIk |
| alkyl-Phe-Phe-CH$_2$CH$_2$-Phe-C≡C-Cl | IIl |
| alkyl-Cyc-CH$_2$CH$_2$-Cyc-Phe-C≡C-Cl | IIm | alkyl-Cyc-Cyc-C≡C-Cl  IIn alkyl-Cyc-CH₂CH₂-Cyc-C≡C-Cl  IIo alkyl-Cyc-CO-O-Cyc-C≡C-Cl  IIp.

6. A liquid crystalline medium according to claim 2, wherein at least one component ia is a compound selected from the sub-formulae I2a to I2q:

alkyl-Phe-Phe-C≡C-F  I2a alkyl-Cyc-Phe-C≡C-F  I2b alkyl-Cyc-Phe-Phe-C≡C-F  I2c alkyl-Cyc-Cyc-Phe-C≡C-F  I2d alkyl-Phe-Phe-Phe-C≡C-F  I2e alkyl-Phe-CH₂CH₂-Phe-C≡C-F  I2f alkyl-Cyc-CH₂CH₂-Phe-C≡C-F  I2g alkyl-Cyc-CO-O-Phe-C≡C-F  I2h alkyl-Phe-CO-O-Phe-C≡C-F  I2i alkyl-Cyc-Phe-C≡C-Phe-C≡C-F  I2j alkyl-Cyc-Phe-CH₂CH₂-Phe-C≡C-F  I2k alkyl-Cyc-Cyc-CH₂CH₂-Phe-C≡C-F  I2l alkyl-Phe-Phe-CH₂CH₂-Phe-C≡C-F  I2m alkyl-Cyc-CH₂CH₂-Cyc-Phe-C≡C-F  I2n alkyl-Cyc-Cyc-C≡C-F  I2o alkyl-Cyc-CH₂CH₂-Cyc-C≡C-F  I2p alkyl-Cyc-CO-O-Cyc-C≡C-F  I2q.

7. A liquid crystalline medium according to claim 2, wherein at least one component is a compound selected from the sub-formulae I4a to I4q:

alkyl-Phe-Phe-C≡C-OCF₃  I4a alkyl-Cyc-Phe-C≡C-OCF₃  I4b alkyl-Cyc-Phe-Phe-C≡C-OCF₃  I4c alkyl-Cyc-Cyc-Phe-C≡C-OCF₃  I4d alkyl-Phe-Phe-Phe-C≡C-OCF₃  I4e alkyl-Phe-CH₂CH₂-Phe-C≡C-OCF₃  I4f alkyl-Cyc-CH₂CH₂-Phe-C≡C-OCF₃  I4g alkyl-Cyc-CO-O-Phe-C≡C-OCF₃  I4h alkyl-Phe-CO-O-Phe-C≡C-OCF₃  I4i alkyl-Cyc-Phe-C≡C-Phe-C≡C-OCF₃  I4j alkyl-Cyc-Phe-CH₂CH₂-Phe-C≡C-OCF₃  I4k alkyl-Cyc-Cyc-CH₂CH₂-Phe-C≡C-OCF₃  I4l alkyl-Phe-Phe-CH₂CH₂-Phe-C≡C-OCF₃  I4m alkyl-Cyc-CH₂CH₂—Cyc-Phe-C≡C-OCF₃  I4n alkyl-Cyc-Cyc-C≡C-OCF₃  I4o alkyl-Cyc-CH₂CH₂-Cyc-C≡C-OCF₃  I4p alkyl-CYC-00-O-Cyc-C≡C-OCF₃  I4q.

* * * * *

UNITED STATES PATENT AND TRADEMARK OFFICE
CERTIFICATE OF CORRECTION

PATENT NO. : 5,188,759
DATED : 2-23-93
INVENTOR(S) : Ekkehard BARTMANN It is certified that error appears in the above-identified patent and that said Letters Patent is hereby corrected as shown below:

Claim 7, Col. 20, line 37:   Delete -OO- and insert

-- CO --

Signed and Sealed this

Twenty-third Day of November, 1993

Attest:

Attesting Officer

BRUCE LEHMAN

Commissioner of Patents and Trademarks